(12) United States Patent
Brereton et al.

(10) Patent No.: US 8,939,934 B2
(45) Date of Patent: Jan. 27, 2015

(54) AUTO-INJECTOR

(75) Inventors: Simon Francis Brereton, Cambridge (GB); Matthew Ekman, Cheshire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 13/995,599

(22) PCT Filed: Dec. 21, 2011

(86) PCT No.: PCT/EP2011/073506
§ 371 (c)(1),
(2), (4) Date: Jun. 19, 2013

(87) PCT Pub. No.: WO2012/085025
PCT Pub. Date: Jun. 28, 2012

(65) Prior Publication Data
US 2013/0289492 A1    Oct. 31, 2013

Related U.S. Application Data

(60) Provisional application No. 61/432,248, filed on Jan. 13, 2011.

(30) Foreign Application Priority Data

Dec. 21, 2010   (EP) ..................................... 10196071

(51) Int. Cl.
*A61M 5/20*   (2006.01)
*A61M 5/32*   (2006.01)
(Continued)

(52) U.S. Cl.
CPC ........... *A61M 5/3202* (2013.01); *A61M 5/2033* (2013.01); *A61M 5/326* (2013.01);
(Continued)

(58) Field of Classification Search
CPC . A61M 5/20; A61M 5/2033; A61M 5/31578; A61M 5/3287; A61M 2005/2013; A61M 2005/206
USPC .................. 604/197, 198, 134–138, 156, 157
See application file for complete search history.

(56) References Cited

U.S. PATENT DOCUMENTS 2,605,766 A    8/1952   Uytenbogaart
8,409,138 B2 *  4/2013  James et al. .................. 604/110
(Continued)

FOREIGN PATENT DOCUMENTS

WO    2009007305 A1    1/2009
WO    2009062508 A1    5/2009

*Primary Examiner* — Kami A Bosworth
*Assistant Examiner* — Glen Janson
(74) *Attorney, Agent, or Firm* — McDonnell Boehnen Hulbert & Berghoff LLP

(57) ABSTRACT

An auto-injector comprising a housing arranged to contain a slidably arranged syringe. The housing having a distal end and a proximal end with an orifice. Spring means is capable of, upon activation: pushing the needle into an advanced position and into an injection site, operating the syringe to inject a dose of medicament, and retracting the syringe. Activating means locks the spring means in a pressurized state prior to manual operation and capable of releasing the spring means for injection. The spring means is a compression spring grounded distally in the housing and proximally bearing against a thrust tube arranged to transmit load from the spring means via a plunger to the syringe and/or the stopper. A tubular syringe carrier is arranged for holding the syringe and supporting it at a proximal end, the syringe and the syringe carrier arranged for joint axial translation.

11 Claims, 7 Drawing Sheets

(51) Int. Cl.
*A61M 5/315* (2006.01)
*A61M 5/50* (2006.01)

(52) U.S. Cl.
CPC .... *A61M5/31578* (2013.01); *A61M 2005/2013* (2013.01); *A61M 2005/206* (2013.01); *A61M 5/5086* (2013.01)
USPC .......................... 604/137; 604/157; 604/198

(56) References Cited

U.S. PATENT DOCUMENTS

2002/0095120 A1  7/2002  Larsen et al.
2010/0280460 A1* 11/2010  Markussen ................... 604/195

* cited by examiner

AUTO-INJECTOR

CROSS REFERENCE TO RELATED APPLICATIONS

The present application is a U.S. National Phase Application pursuant to 35 U.S.C. §371 of International Application No. PCT/EP2011/073506 filed Dec. 21, 2011, which claims priority to European Patent Application No. 10196071.4 filed Dec. 21, 2010 and U.S. Provisional Patent Application No. 61/432,248 filed Jan. 13, 2011. The entire disclosure contents of these applications are herewith incorporated by reference into the present application.

FIELD OF INVENTION

The invention relates to an auto-injector for administering a dose of a liquid medicament according to the preamble of claim 1.

BACKGROUND

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an under dose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

US 2002/0095120 A1 discloses an automatic injection device which automatically injects a pre-measured quantity of fluid medicine when a tension spring is released. The tension spring moves an ampoule and the injection needle from a storage position to a deployed position when it is released. The content of the ampoule is thereafter expelled by the tension spring forcing a piston forward inside the ampoule. After the fluid medicine has been injected, torsion stored in the tension spring is released and the injection needle is automatically retracted back to its original storage position.

SUMMARY

It is an object of the present invention to provide an improved auto-injector.

The object is achieved by an auto-injector according to claim 1.

Preferred embodiments of the invention are given in the dependent claims.

In the context of this specification the term proximal refers to the direction pointing towards the patient during an injection while the term distal refers to the opposite direction pointing away from the patient. The terms clockwise and counter-clockwise refer to rotations seen from a distal end of the auto-injector.

An auto-injector for delivering a liquid medicament according to the invention comprises—an elongate housing arranged to contain a syringe with a hollow injection needle and a stopper for sealing the syringe and displacing the medicament. The housing has a distal end and a proximal end with an orifice intended to be applied against an injection site, e.g. a patient's skin, wherein the syringe is slidably arranged with respect to the housing, spring means capable of, upon activation:
pushing the needle from a covered position inside the housing into an advanced position through the orifice and past the proximal end for insertion into an injection site,
operating the syringe to inject the dose of medicament, and
retracting the syringe with the needle into the covered position after at least partially delivering the medicament,
activating means arranged to lock the spring means in a pressurized state prior to manual operation and capable of, upon manual operation, releasing the spring means for injection.

The spring means is a compression spring grounded distally in the housing and proximally bearing against a thrust tube arranged to transmit load from the spring means via a plunger to the syringe and/or the stopper. A tubular syringe carrier is arranged for holding the syringe and supporting it at its proximal end, the syringe and the syringe carrier arranged for joint axial translation. The thrust tube is arranged to be rotationally constrained relative to the housing. The thrust tube and the plunger exhibit corresponding first and second threads having a first direction, e.g. right-handed or left-handed arranged to be engaged at least in an initial state. The plunger is rotationally constrained in the initial state, during needle insertion and during injection thus preventing it from decoupling from the thrust tube. The plunger is arranged to be rotationally released upon removal of the auto-injector from the injection site resulting in rotation of the plunger and consequently disengagement of the corresponding first and second threads. The thrust tube is arranged to consequently translate further under load of the compression spring in such a manner that the second thread engages a corresponding third thread of a retract collar which is engaged to the syringe carrier by corresponding fourth and fifth threads having the opposite direction of the first direction so that continued translation of the thrust tube in proximal direction results in rotation of the retract collar and translation of the syringe carrier in distal direction for needle retraction.

Effectively, the thrust tube and the plunger act like a two-part plunger. Their threaded connection allows them to drive various control elements and separate under force of the single compression spring. This is an improvement over conventional art auto-injectors as the injection can be prematurely halted, retracting the needle and preventing any further drug delivery, immediately as the auto-injector is lifted from the injection site. The auto-injector according to the invention has a particularly low part count.

The activating means may comprise a skin trigger sleeve telescoped in the housing, translatable in longitudinal direction between an advanced position protruding beyond the proximal end of the housing and a depressed position further into the housing. The skin trigger sleeve is biased towards the advanced position, e.g. by a trigger spring which may be integrally moulded with the skin trigger sleeve. In the initial state the thrust tube is arranged to be locked for preventing translation. The skin trigger sleeve is arranged to release the thrust tube on translation into the depressed position for starting an injection cycle. Triggering the injection by means of the skin trigger sleeve facilitates operation for users with reduced dexterity since grabbing the auto-injector and pushing it against the skin requires less dexterity than operating a trigger button.

The thrust tube may be connected to the housing by at least one bayonet pin engaged in at least one bayonet track. In the initial state the skin trigger sleeve, the syringe carrier and the plunger are rigidly connected for joint translation and rotation so that translation of the skin trigger sleeve into the depressed position results in translation of the plunger relative to the thrust tube. Due to the threaded engagement of the plunger and the thrust tube translation of the plunger results in rotation of the thrust tube about a small angle so that the bayonet pin is rotated out of a circumferential portion into a longitudinal portion of the bayonet track thus allowing translation of the thrust tube under load of the compression spring.

A lock may be arranged partially inside a distal end of the skin trigger sleeve around a piston rod of the plunger. The lock may be axially coupled to the syringe carrier. The piston rod is keyed into the lock for joint rotation. The lock comprises at least one resilient arm, preferably at least two resilient arms engageable in a circumferential notch in the piston rod or behind a shoulder on the piston rod in a manner to couple the piston rod and the lock for joint translation. The resilient arm is arranged to disengage from the circumferential notch due to ramped engagement under axial load. The resilient arm is arranged to be outwardly supported by the skin trigger sleeve for preventing outward deflection thus coupling the plunger to the syringe carrier for needle insertion. At least one aperture is arranged in the skin trigger sleeve for allowing outward deflection of the resilient arm upon the needle reaching an injection depth.

The resilient arm and the skin trigger sleeve may be arranged to be splined to each other for joint rotation, wherein the spline engagement is interrupted by the aperture thus allowing rotation of the lock relative to the skin trigger sleeve upon the needle reaching the injection depth. Prior to this the resilient arm remains splined to the skin trigger sleeve.

The aperture may be arranged as an L-shaped aperture, wherein the spline engagement of the resilient arm and the skin trigger sleeve is interrupted by a second circumferential portion of the aperture, wherein a second longitudinal portion of the aperture is arranged to allow translation of the lock with the outwardly deflected and rotated resilient arm in distal direction relative to the skin trigger sleeve. Thus, upon rotation of the lock with the resilient arm into the second longitudinal portion the lock, the syringe carrier, the syringe and the needle may be retracted into a needle safe position.

At least one lock boss may be arranged on the lock for abutting against at least one stop on the skin trigger sleeve upon rotation of the lock relative to the skin trigger sleeve thus preventing complete unscrewing of the plunger from the thrust tube. The plunger is thus prepared for being unscrewed from the thrust tube.

The stop on the skin trigger sleeve may be arranged to be translated out of the way of the lock boss on removal of the auto-injector from the injection site and consequent translation of the skin trigger sleeve back into the advanced position so as to allow further rotation of the lock with the plunger for allowing complete unscrewing of the plunger and the thrust tube in order to allow the thrust tube to decouple from the plunger, translate further, engage the retract collar and retract the needle.

The retract collar may be arranged to be coupled to the skin trigger sleeve for joint axial translation by a bayonet connection between an outward boss and an inward boss in the initial state. Upon release of the compression spring the retract collar is arranged to be rotated due to the corresponding fourth and fifth threads and the load of the compression spring transmitted via the plunger, the lock and the syringe carrier so as to disengage the bayonet connection and axially decouple the retract collar from the skin trigger sleeve. The bayonet feature ensures the starting position for the retract collar after the skin trigger sleeve has been moved in the distal direction.

A first detent may be arranged for obstructing disengagement of the bayonet connection between the retract collar and the syringe carrier. A second detent may be arranged for obstructing disengagement of the bayonet pin on the thrust tube from the circumferential portion. The first detent is configured to require more torque to be overcome than the second detent. The boss/detent between the retract collar and skin trigger sleeve allows the auto-injector to be triggered by pressing the skin trigger sleeve. Prior to use the plunger is rigidly connected to the syringe carrier by the lock. In order to trigger the auto-injector the plunger must be moved backwards. This movement is resisted by the second detent. The first detent ensures that the carrier moves backwards with the skin trigger sleeve, rather than the retract collar rotating. Once the second detent has been released, the first detent releases to allow the carrier to advance.

The aperture may comprise a distal edge arranged to be engaged by the outwardly deflected resilient arm upon needle retraction so as to also retract the skin trigger sleeve into the depressed position. This may be used to indicate that the auto-injector has been used so the user is kept from attempting to use it again.

The auto-injector may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a protein, antibodies and complex carbohydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
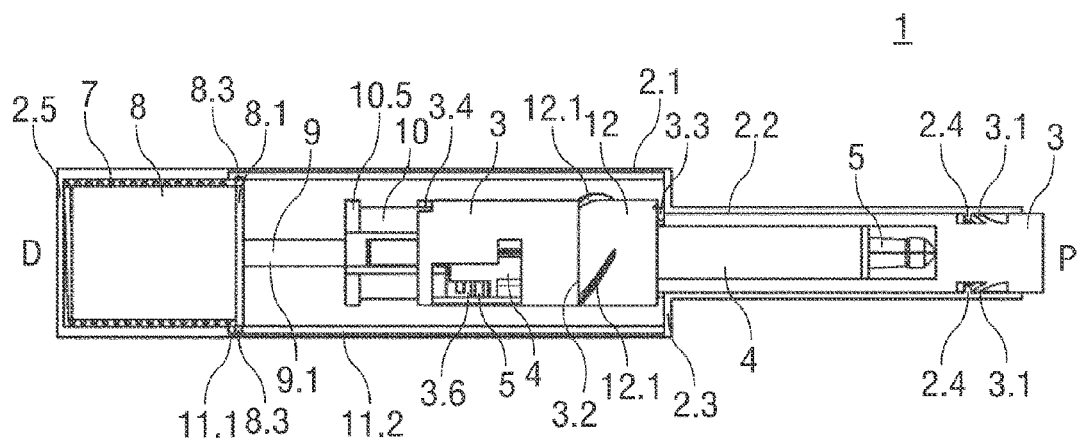
FIG. 1 is a partial longitudinal section of an auto-injector in an initial as delivered state prior to an injection.

FIG. 1 shows a longitudinal section of an auto-injector 1. A housing 2 of the auto-injector 1 comprises a distal portion 2.1 and a proximal portion 2.2 with a first shoulder 2.3 in between, both portions 2.1, 2.2 essentially cylindrical, wherein the distal portion 2.1 has a substantially greater diameter than the proximal portion 2.2.

The auto-injector 1 comprises only a few parts made from a plastics material. A skin trigger sleeve 3 is telescoped in the housing 2 translatable in a longitudinal direction of the auto-injector 1, wherein rotation of the skin trigger sleeve 3 relative to the housing 2 is prevented by a splined engagement (not illustrated).

Two trigger spring arms 3.1 are integrally moulded with the skin trigger sleeve 3 near the proximal end in a manner to bias the skin trigger sleeve 3 in proximal direction P against a rib 2.4 in the housing 2. When the skin trigger sleeve 3 is translated in a distal direction D with respect to the housing 2, the trigger springs 3.1 are resiliently deformed.

A syringe carrier 4 is telescoped and keyed into the skin trigger sleeve 3 so as to allow relative translation and prevent relative rotation. The syringe carrier 4 is arranged to hold a syringe 5 and support it at a proximal end in such a manner that the syringe 5 never moves relative to the syringe carrier 4. The syringe carrier 4 is translatable within the skin trigger sleeve 3, whereby rotation of the syringe carrier 4 relative to the skin trigger sleeve 3 is prevented. A hollow injection needle 6 is attached to the syringe 5. The syringe 5 contains a dose of medication M intended to be delivered to a patient through the needle 6.

A drive means 7 is arranged for advancing the syringe 5 and the needle 6 for insertion of the needle into an injection site, e.g. a patient's skin, for delivering the dose of medicament and for retracting the needle 6 for post injection needle safety. The drive means 7 has the shape of a single compression spring 7 arranged in the distal portion 2.1. A thrust tube 8 is arranged in the distal portion 2.1 inside the compression spring 7, the thrust tube 8 having a thrust collar 8.1 at its proximal end. The compression spring 7 is arranged to distally bear against a distal end face 2.5 on the housing 2 and proximally against the thrust collar 8.1.

Figure 2:
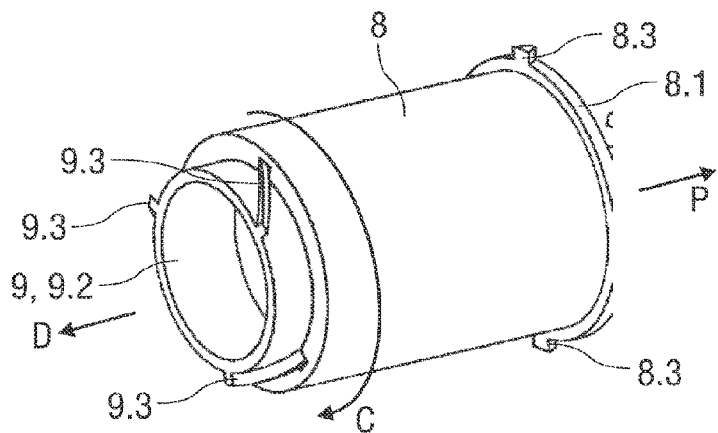
FIG. 2 is an isometric view of a threaded connection between a thrust tube and a plunger of the auto-injector.

A plunger 9 for transmitting load from the compression spring 7 to the syringe 5 and to a stopper (illustrated in FIG. 10) in the syringe 5 is initially arranged partially inside the thrust tube 8. The plunger 9 comprises a proximal piston rod 9.1 and a distal threaded part 9.2 (see FIG. 2) with an external first thread 9.3 engaged in an internal second thread 8.2 (see FIG. 3) in the thrust tube 8 in the initial state.

Figure 9:
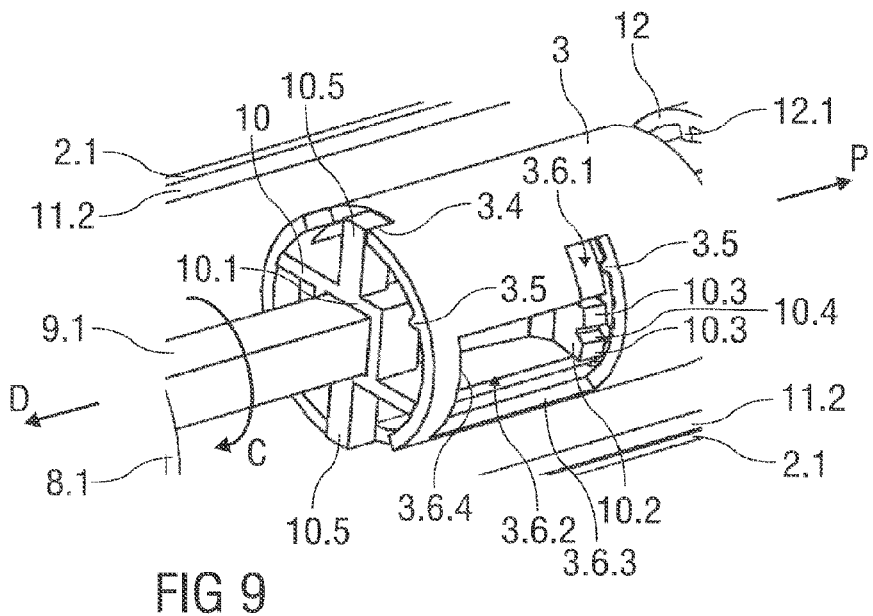
FIG. 9 is an isometric detail view of a lock for controlling relative rotation between the skin trigger sleeve and a piston rod immediately prior to the needle reaching an injection depth.
Figure 10:
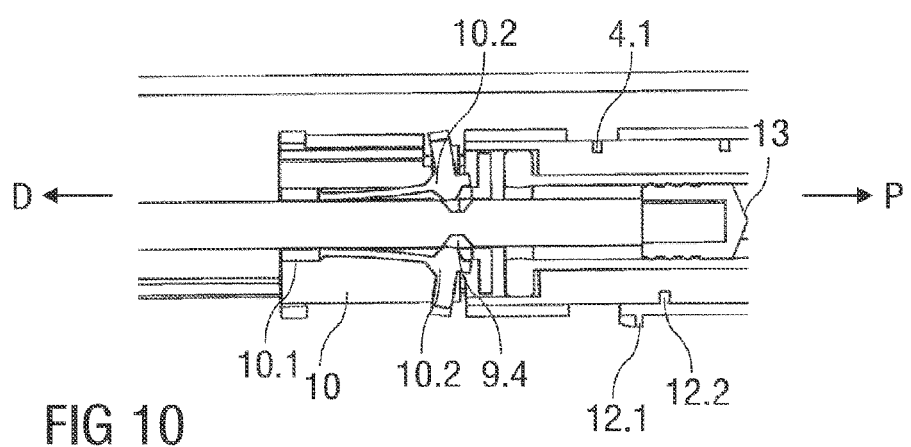
FIG. 10 is a longitudinal section detail of the lock decoupling the piston rod from the syringe carrier and coupling it to a stopper for injection.

A lock 10 is arranged partially inside a distal end of the skin trigger sleeve 3 around the piston rod 9.1 which is keyed into the lock 10 so they cannot rotate relative to each other. For this purpose the piston rod 9.1 and the lock 10 exhibit corresponding non-circular cross sections (see FIG. 9). In the illustrated embodiment the cross sections are square but they could likewise have a different non-circular shape. The lock 10 comprises a keyhole part 10.1 for keying with the piston rod 9.1 and two resilient arms 10.2 extending in proximal direction P from the keyhole part 10.1. In the initial state the resilient arms 10.2 are engaged in a circumferential notch 9.4 in the piston rod 9.1 in a manner to couple the piston rod 9.1 and the lock 10 for joint translation. (see FIG. 10) The lock 10 is axially coupled to the syringe carrier 4. The resilient arms 10.2 are arranged to disengage from the circumferential notch 9.4 due to ramped engagement under axial load. FIG. 10 shows the details of the lock 10 axially disengaged from the piston rod 9.1. The resilient arms 10.2 respectively have an arcuate outer surface 10.3 having roughly the radius of an inner surface of the skin trigger sleeve 3 in the distal part where the lock 10 is arranged. In the initial state a longitudinal ridge 3.5 on the inner surface of the skin trigger sleeve 3 is engaged in a longitudinal notch 10.4 in the arcuate outer surface 10.3 so as to obstruct clockwise rotation (seen from the distal end D) of the lock 10 relative to the skin trigger sleeve 3. In this relative angular position the arcuate outer surface 10.3 is at least partially covered by the skin trigger sleeve 3 preventing outward deflection of the resilient arms 10.2 and thus axial disengagement of the lock 10 from the piston rod 9.1. A longitudinal slot 4.2 in the syringe carrier 4 is engaged with a more proximal part of the longitudinal ridge 3.5 for preventing rotation of the syringe carrier 4 relative to the skin trigger sleeve 3.

Figure 3:
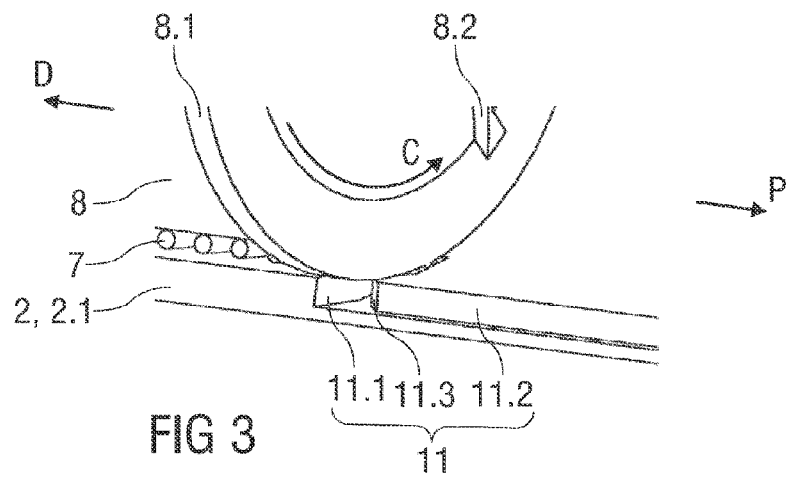
FIG. 3 is an isometric view of a bayonet coupling between the thrust tube and the housing of the auto-injector.

In the initial state the thrust tube 8 is prevented from translating in proximal direction P as it is connected to the housing 2 with a bayonet (see FIG. 3). For this purpose two bayonet pins 8.3 are circumferentially arranged on the thrust collar 8.1. The bayonet pins 8.3 are initially held in a first circumferential portion 11.1 of a bayonet track 11. When rotated by a small angle the bayonet pin 8.3 leaves the first circumferential portion 11.1 and enters a first longitudinal portion 11.2 parallel to the longitudinal axis of the auto-injector 1.

Figure 5:
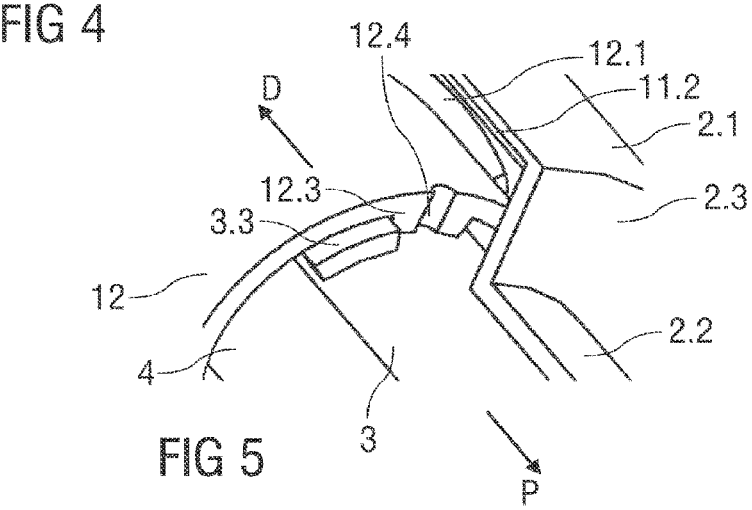
FIG. 5 is an isometric detail view of a retract collar rotated for releasing it from the skin trigger sleeve for independent translation in longitudinal direction.
Figure 6:
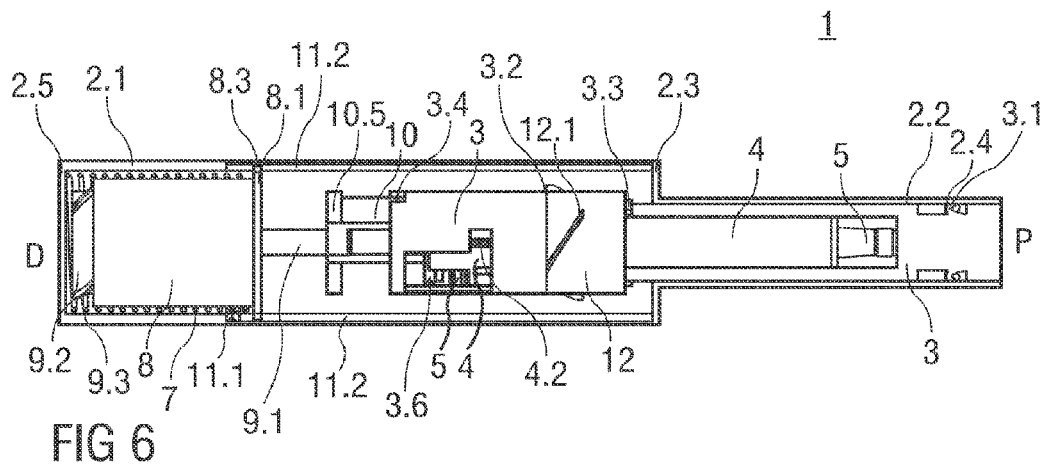
FIG. 6 is a partial longitudinal section of the auto-injector with the retract collar rotated for releasing it from the skin trigger sleeve for independent translation in longitudinal direction.

A retract collar 12 is arranged in the distal portion 2.1. In the initial state, the retract collar 12 is arranged over the skin trigger sleeve 3 and the syringe carrier 4 which are keyed into each other. The retract collar 12 has an external third thread 12.1 arranged to allow engagement to the thrust tube 8. In the initial state the retract collar 12 is distally abutted against a second shoulder 3.2 in the skin trigger sleeve 3. Proximally, an inward boss 12.3 on the retract collar 12 is engaged behind an outward boss 3.3 on the skin trigger sleeve 3 in such a manner that the retract collar 12 cannot translate relative to the skin trigger sleeve 3 (FIG. 5 shows the bosses 3.3, 12.3 released.).

In the initial state the skin trigger sleeve 3, the retract collar 12, the syringe carrier 4, the lock 10, and the plunger 9, i.e. all parts except the housing 2 and the thrust tube 8 are rigidly connected.

Figure 4:
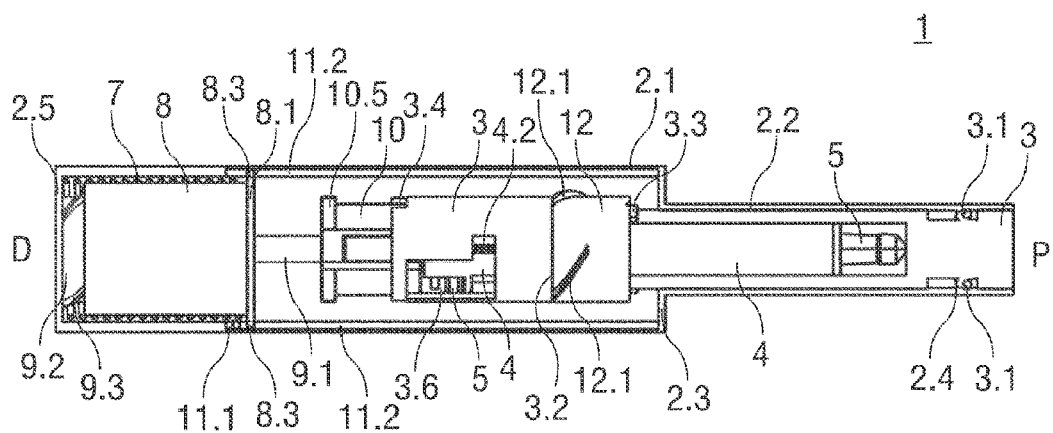
FIG. 4 is a partial longitudinal section of the auto-injector with a depressed skin trigger sleeve.

To fire the auto-injector 1, it must be pushed with the proximal end P against the injection site, translating the skin trigger sleeve 3 in distal direction relative the housing 2 (see FIG. 4). As all the parts except the housing 2 and the thrust tube 8 are rigidly connected, translating the skin trigger sleeve 3 also causes translation of the retract collar 12, the syringe carrier 4, the lock 10, and the plunger 9. As the thrust tube 8 and plunger 9 are joined with the threaded connection (see FIG. 2), pushing the plunger 9 in distal direction D forces the thrust tube 8 to rotate counter-clockwise (seen from the distal end D), releasing its bayonet connection to the housing 2, i.e. the bayonet pin 8.3 is rotated out of the first circumferential portion 11.1 into the first longitudinal portion 11.2 of the bayonet track 11 (see FIG. 4). The compression spring 7 is thus released.

The plunger 9 and lock 10 are rotationally constrained at this point by a spline to the skin trigger sleeve 3 so the plunger 9 is prevented from rotating with the thrust tube 8. The release of this constraint is illustrated in FIG. 9.

The retract collar 12 has an internal fourth thread 12.2 engaged in an external fifth thread 4.1 in the syringe carrier 4 (see FIG. 10). The user keeps pressing the auto-injector 1 against the injection site thus holding the skin trigger sleeve 3 back in its distal position. The compression spring 7 is trying to push the thrust tube 8, plunger 9, lock 10, syringe carrier 4, syringe 5 and injection needle 6 in proximal direction P. As they translate, the retract collar 12 rotates releasing the inward boss 12.3 from behind the outward boss 3.3 thus allowing translation of the retract collar 12 in proximal direction P relative to the skin trigger sleeve 3 (see FIG. 5). A first detent 12.4 obstructing disengagement of the inward boss 12.3 from the outward boss 3.3 is configured to require more torque for allowing disengagement than a second detent 11.3 obstructing the passage of the bayonet pin 8.3 from the first circumferential portion 11.1 to the longitudinal section 11.2, forcing the order in which they release, first the bayonet connection of the thrust tube 8 and then the retract collar 12 from the skin trigger sleeve 3. The force transfer between the skin trigger sleeve 3 and plunger 9 to release the firing mechanism is: skin trigger sleeve 3, retract collar 12, syringe carrier 4, lock 10, plunger 9. The first detent 12.4 between the retract collar 12 and skin trigger sleeve 3 releases when the plunger 9 starts pushing the syringe carrier 4 forwards. The user will resolve the load required to overcome this detent 12.4. The lock 10 is never rigidly fixed to the trigger sleeve 3, they are initially connected through the syringe carrier 4 and retraction collar 12.

Figure 7:
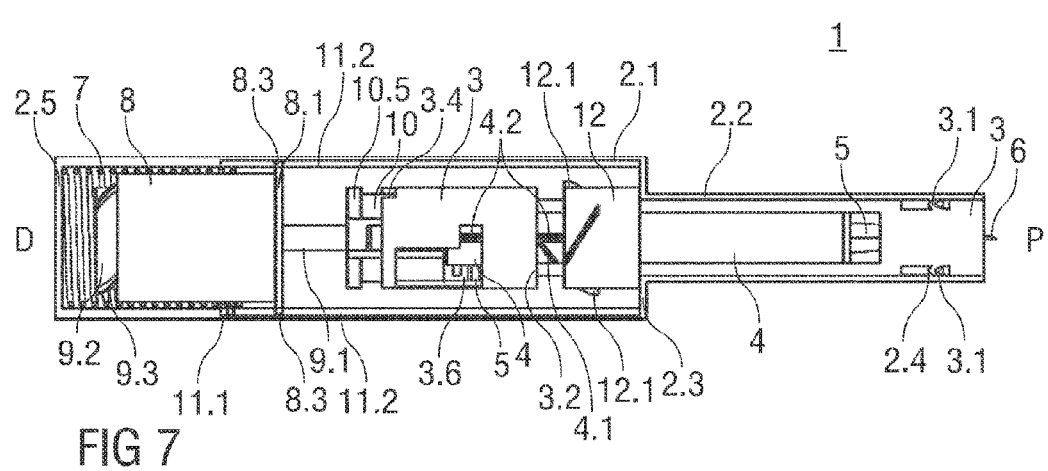
FIG. 7 is a partial longitudinal section of the auto-injector during needle insertion into an injection site as the retract collar proximally abuts against the housing.
Figure 8:
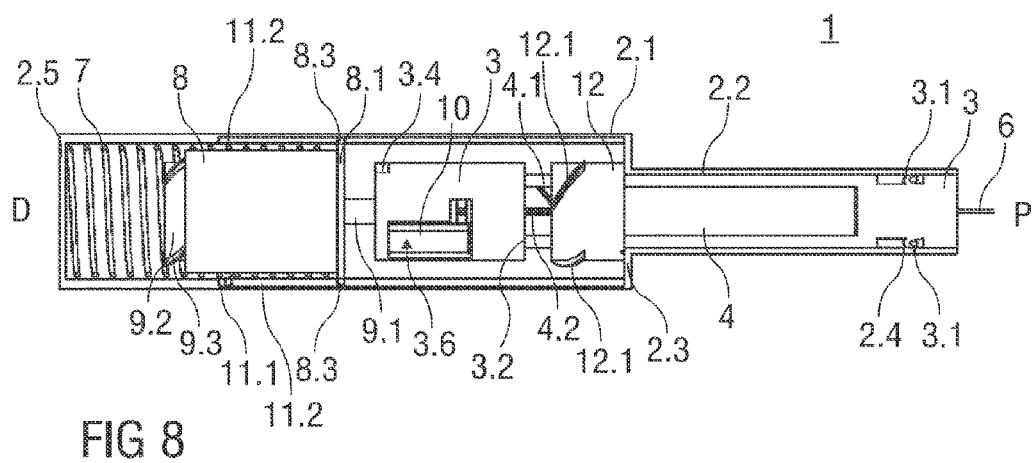
FIG. 8 is a partial longitudinal section of the auto-injector during needle insertion with the needle further advanced, wherein the retract collar is rotated by an advancing syringe carrier.

The syringe carrier 4 continues translating in proximal direction P relative to the housing 2 and skin trigger sleeve 3 thereby advancing the needle 6 beyond the proximal end P and inserting it into the injection site. As the retract collar 12 proximally abuts against the first shoulder 2.3 during that motion (see FIG. 7) it rotates freely due to its threaded connection to the still moving syringe carrier 4 until a front stop on the syringe carrier 4 hidden under the retract collar 12 hits the first shoulder 2.3 (see FIG. 8).

As the thrust tube 8 is translated a torque is applied to the thrust tube 8 in counter-clockwise direction and to the plunger 9 in clockwise direction due to their threaded connection. However, the thrust tube 8 is prevented from rotating by the bayonet pins 8.3 engaged in the first longitudinal portion 11.2 of the bayonet track 11. The plunger 9 is prevented from rotating due to its keyed engagement in the lock 10 and the longitudinal ridge 3.5 engaged in the longitudinal notch 10.4 (see FIG. 9). Hence, the threaded connection between the thrust tube 8 and the plunger 9 can not undo.

Immediately prior to the needle 6 reaching an injection depth, the lock 10 advancing relative to the skin trigger sleeve 3 reaches a second circumferential portion 3.6.1 of an L-shaped aperture 3.6 in the skin trigger sleeve 3 interrupting the longitudinal ridge 3.5. The resilient arms 10.2 are no longer outwardly supported by the skin trigger sleeve 3 but deflected outwards due to their ramped engagement to the piston rod 9.1 under load of the compression spring 7 decoupling the piston rod 9.1 from the lock 10 and the syringe carrier 4 and allowing it to push directly on the stopper 13 instead (see FIG. 10) for injecting the medicament. Furthermore, due to the interruption of the longitudinal ridge 3.5 the lock 10 is rotationally released from the piston rod 9.1. The clockwise torque on the plunger 9 rotates the lock 10 until a lock boss 10.5 on the lock 10 abuts against a stop 3.4 in the skin trigger sleeve 3 in clockwise direction. A second longitudinal portion 3.6.2 of the L-shaped aperture is arranged to allow translation of the lock 10 in distal direction D relative to the skin trigger sleeve 3 in this state with the outwardly deflected resilient arms 10.2. This situation is illustrated in FIG. 9.

Figure 11:
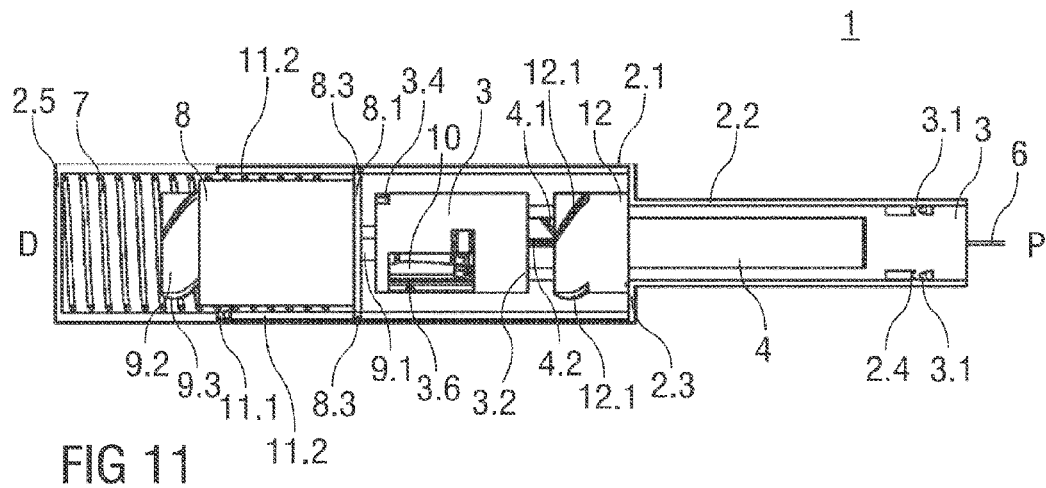
FIG. 11 is a partial longitudinal section of the auto-injector with the needle fully inserted and starting to inject.

The short rotation of the lock 10 unscrews the plunger 9 further from the thrust tube 8 (see FIG. 11).

Figure 12:
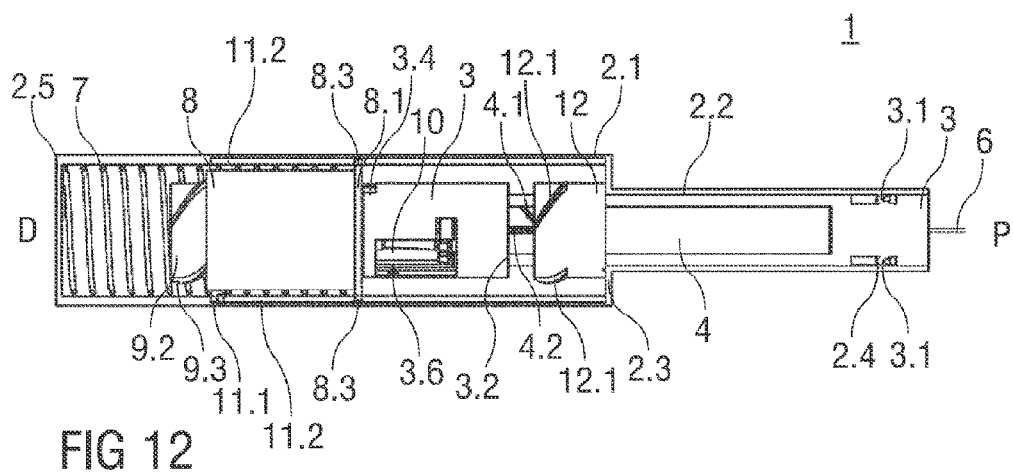
FIG. 12 is a partial longitudinal section of the auto-injector mid injection.

FIG. 12 shows the auto-injector 1 mid injection. Only a small quantity has been injected in this figure to allow the details to be seen.

Figure 13:
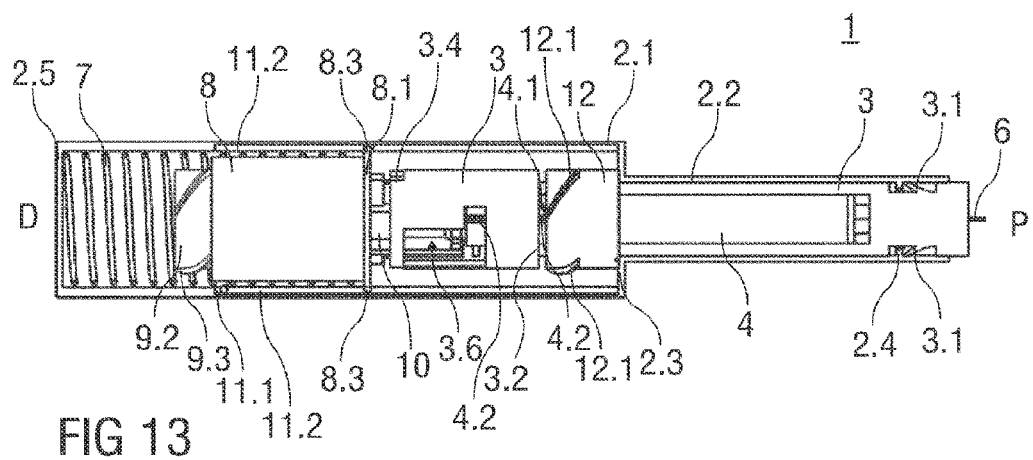
FIG. 13 is a partial longitudinal section of the auto-injector removed from the injection site mid injection allowing translation of the skin trigger sleeve out of the housing.

If the user lifts the auto-injector 1 off the injection site during the injection, the skin trigger sleeve 3 translates in proximal direction P under the force of the trigger spring 3.1 (see FIG. 13). Hence, the lock boss 10.5 on the lock 10 comes clear from the stop 3.4 so the lock 10 is released and allowed to rotate further in clockwise direction until the outwardly deflected resilient arm 10.2 abuts against a clockwise edge 3.6.3 of the second longitudinal portion 3.6.2 of the L-shaped aperture (see FIGS. 9 and 14).

Due to the hydrostatic resistance of the liquid medicament being forced through the narrow fluid channel of the injection needle 6 it is easier for the threaded part 9.2 of the plunger 9 to screw out of the thrust tube 8, than to push the medicament out of the syringe 5. Hence, the threaded part 9.2 of the plunger 9 is completely screwed out of the thrust tube 8 (see FIG. 14).

Figure 15:
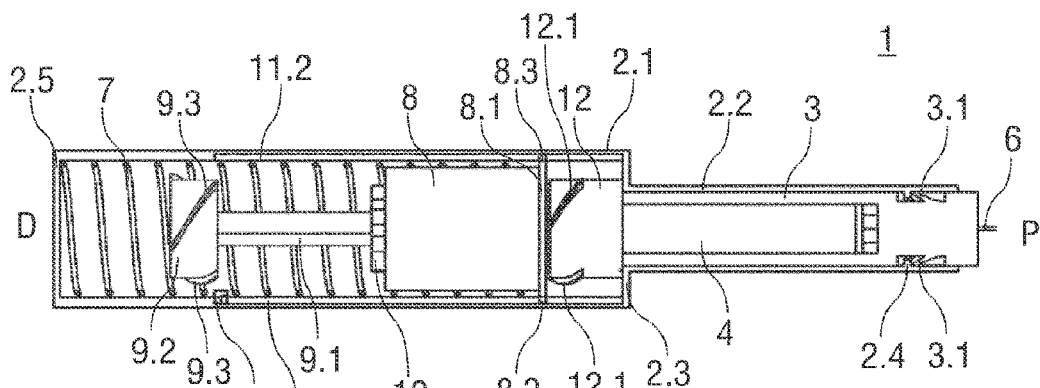
FIG. 15 is a partial longitudinal section of the auto-injector with the thrust tube advanced in the proximal direction reaching the retract collar.

No longer restricted by the plunger 9 the thrust tube 8 is advanced further in proximal direction P until it reaches the retract collar 12 (see FIG. 15). The internal second thread 8.2 of the thrust tube 8 engages the external third thread 12.1 of the retract collar 12 and the retract collar 12 is rotated as the thrust tube 8 is further advanced. The positions of the threads 8.2, 12.1 are defined as the thrust tube 8 is splined into the housing 2 by the bayonet pins 8.3 engaged in the first longitudinal portion 11.2 of the bayonet track 11 and as the retract collar 12 is threaded onto the syringe carrier 4 which is against the housing 2. A funnel type lead in may be arranged at the proximal end of the internal second thread 8.2 to make up for tolerances ensuring that the second thread 8.2 and the third thread 12.1 always engage.

Figure 16:
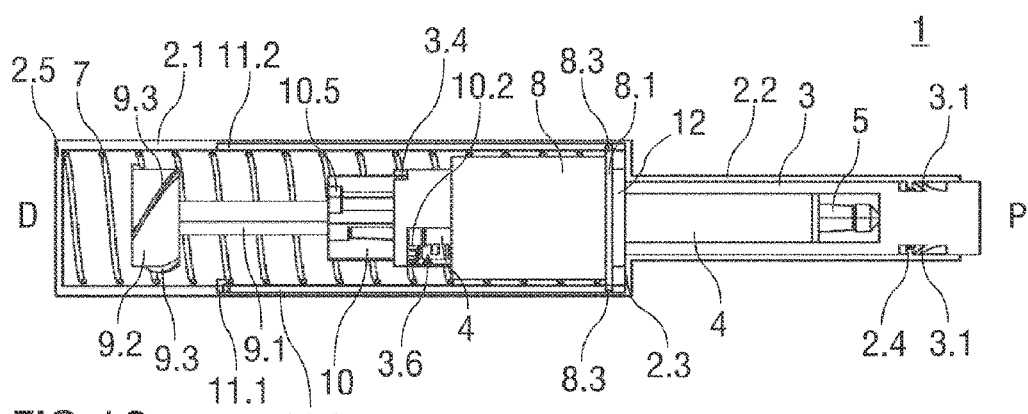
FIG. 16 is a partial longitudinal section of the auto-injector during needle retraction.

The threaded connection between the internal fourth thread 12.2 of the retract collar 12 and the external fifth thread 4.1 on the syringe carrier 4 is in the opposite direction of the other threaded connections 8.2, 9.3; 8.2, 12.1. Thus, clockwise rotation of the retract collar 12 due to the thrust tube 8 advancing in proximal direction P is converted into a translation of the syringe carrier 4 in distal direction D. The translating syringe carrier 4 takes the lock 10, the syringe 5 and needle 6 with it, retracting the needle 6 from the injection site and hiding it inside the housing 2 (see FIG. 16).

Figure 17:
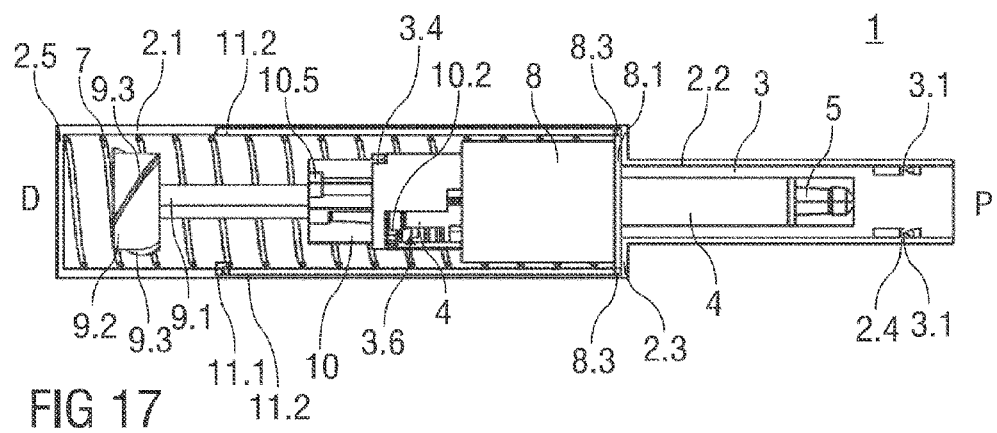
FIG. 17 is a partial longitudinal section of the auto-injector with the lock retracting the skin trigger sleeve.

As the resilient arms 10.2 of the lock 10 reach a distal edge 3.6.4 of the second longitudinal portion 3.6.2 of the L-shaped aperture 3.6 during translation in distal direction D the translating lock 10 catches the skin trigger sleeve 3 pulling it into the housing 2 to indicate that the auto-injector 1 has been used (see FIG. 17).

Figure 18:
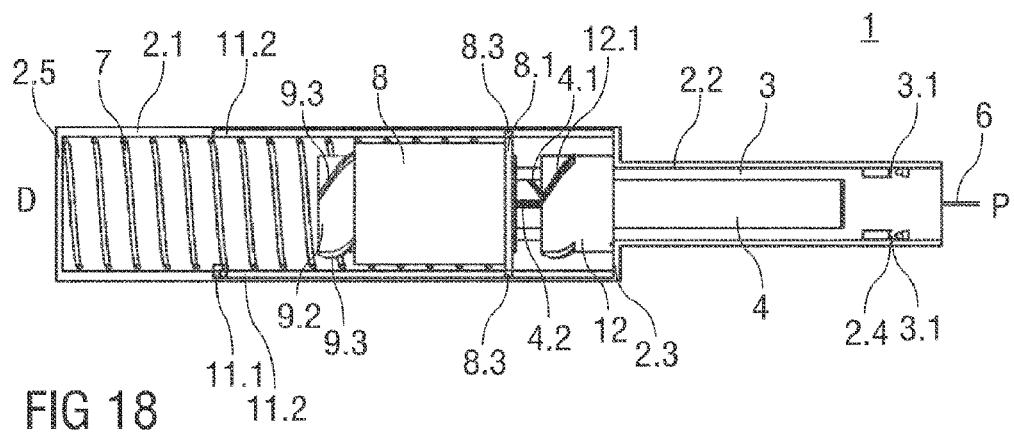
FIG. 18 is a partial longitudinal section of the auto-injector removed from the injection site after full delivery allowing translation of the skin trigger sleeve out of the housing.

If the user keeps the auto-injector 1 pressed against the injection site until the full dose contained in the syringe 5 has been delivered the thrust tube 8, the plunger 9 and the stopper 13 continue their motion from the position shown in FIG. 12 into the position shown in FIG. 18.

If the user lifts the auto-injector 1 off the injection site, the skin trigger sleeve 3 translates in proximal direction P under the force of the trigger spring 3.1 as in FIG. 13. Hence, the lock boss 10.5 on the lock 10 comes clear from the stop 3.4 so the lock 10 is released and allowed to rotate further in clockwise direction until the outwardly deflected resilient arm 10.2 abuts against a clockwise edge 3.6.3 of the second longitudinal portion 3.6.2 of the L-shaped aperture as in FIG. 14.

Figure 14:
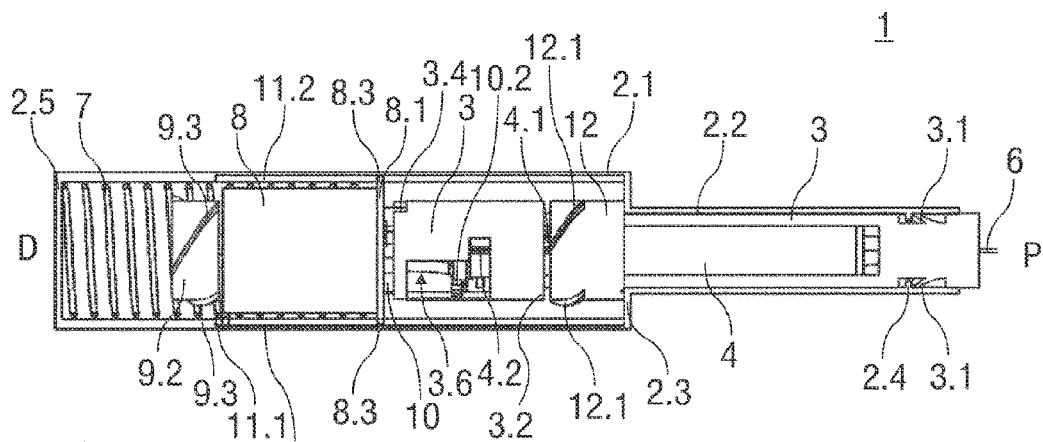
FIG. 14 is a partial longitudinal section of the auto-injector with the plunger screwed completely out of the thrust tube.

Continued translation of the thrust tube 8 screws the threaded part 9.2 of the plunger 9 completely out of the thrust tube 8 since the stopper 13 and piston rod 9.1 of the plunger 9 have bottomed out in the syringe 5 and cannot move further. The situation is similar to what is illustrated in FIG. 14.

No longer restricted by the plunger 9 the thrust tube 8 is advanced further in proximal direction P until it reaches the retract collar 12 as in FIG. 15. The internal second thread 8.2 of the thrust tube 8 engages the external third thread 12.1 of the retract collar 12 and the retract collar 12 is rotated as the thrust tube 8 is further advanced. The positions of the second thread 8.2 relative to the third thread 12.1 is defined as the thrust tube 8 is splined into the housing 2 by the bayonet pins 8.3 engaged in the first longitudinal portion 11.2 of the bayonet track 11 and as the retract collar 12 is threaded onto the syringe carrier 4 which is against the housing 2. A funnel type lead in may be arranged at the proximal end of the internal second thread 8.2 to make up for tolerances ensuring that the threads 8.2, 12.1 always engage.

The threaded connection between the internal fourth thread 12.2 of the retract collar 12 and the external fifth thread 4.1 on the syringe carrier 4 is in the opposite direction of the other threaded connections 8.2, 9.3; 8.2, 12.1. Thus, clockwise rotation of the retract collar 12 due to the thrust tube 8 advancing in proximal direction P is converted into a translation of the syringe carrier 4 in distal direction D. The translating syringe carrier 4 takes the lock 10, the syringe 5 and needle 6 with it, retracting the needle 6 from the injection site and hiding it inside the housing 2 (similar to FIG. 16).

Figure 19:
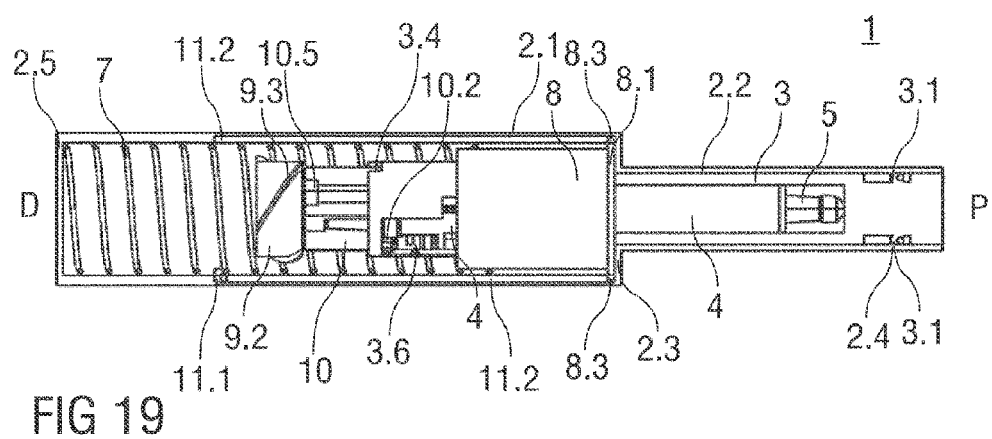
FIG. 19 is a partial longitudinal section of the auto-injector with the needle and skin trigger sleeve retracted after full delivery.

As the resilient arms 10.2 of the lock 10 reach the distal edge 3.6.4 of the second longitudinal portion 3.6.2 of the L-shaped aperture 3.6 during translation in distal direction D the translating lock 10 catches the skin trigger sleeve 3 pulling it into the housing 2 to indicate that the auto-injector 1 has been used (see FIG. 19).

In the illustrated embodiment the threaded connections 8.2, 9.3; 8.2, 12.1 and 12.2, 4.1 are multi-start threads. However, single start threads may also be applied.

The auto-injector 1 may be configured to have a two-stage triggering mechanism, e.g. by a detent obstructing translation of skin trigger sleeve 3.

The sense of rotation of the rotating components was illustrated by way of example. The auto-injector 1 may easily be designed to have these components rotate in the opposite sense. This would require the threaded connections 8.2, 9.3; 8.2, 12.1 and 12.2, 4.1 to have the opposite sense and the lock 10 and the L-shaped aperture 3.6 to be adequately modified.

The auto-injector 1 may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a protein, antibodies and complex carbohydrates.

The invention claimed is:

1. An auto-injector for delivering a liquid medicament, comprising an elongate housing arranged to contain a syringe with a hollow injection needle and a stopper for sealing the syringe and displacing the medicament, the housing having a distal end and a proximal end with an orifice intended to be applied against an injection site, wherein the syringe is slidably arranged with respect to the housing,
   spring means capable of, upon activation:
   pushing the needle from a covered position inside the housing into an advanced position through the orifice and past the proximal end for insertion into an injection site,
   operating the syringe to inject a dose of medicament, and
   retracting the syringe with the needle into the covered position after at least partially delivering the medicament,
   activating means arranged to lock the spring means in a pressurized state prior to manual operation and capable of, upon manual operation, releasing the spring means for injection,
   wherein the spring means is a compression spring grounded distally in the housing and proximally bearing against a thrust tube arranged to transmit load from the spring means via a plunger to the syringe and/or the stopper,
   wherein a tubular syringe carrier is arranged for holding the syringe and supporting it at a proximal end, the syringe and the syringe carrier arranged for joint axial translation,
   wherein the thrust tube is arranged to be rotationally constrained relative to the housing, wherein the thrust tube and the plunger exhibit corresponding first and second threads having a first direction arranged to be engaged at least in an initial state, wherein the plunger is rotationally constrained in the initial state, during needle insertion and during injection, wherein the plunger is arranged to be rotationally released upon removal of the auto-injector from the injection site resulting in rotation of the plunger and consequently disengagement of the corresponding first and second threads, wherein the thrust tube is arranged to consequently translate further under load of the compression spring in such a manner that the second thread engages a corresponding third thread of a retract collar which is engaged to the syringe carrier by corresponding fourth and fifth threads having an opposite direction of the first direction so that continued translation of the thrust tube in proximal direction results in rotation of the retract collar and translation of the syringe carrier in distal direction for needle retraction.

2. The auto-injector according to claim 1, characterized in that the activating means comprise a skin trigger sleeve telescoped in the housing, translatable in longitudinal direction between an advanced position protruding beyond the proximal end of the housing and a depressed position further into the housing, wherein the skin trigger sleeve is biased towards the advanced position, wherein in the initial state the thrust tube is arranged to be locked for preventing translation and wherein the skin trigger sleeve is arranged to release the thrust tube on translation into the depressed position for starting an injection cycle.

3. The auto-injector according to claim 2, characterized in that the thrust tube is connected to the housing by at least one bayonet pin engaged in at least one bayonet track, wherein in the initial state the skin trigger sleeve, the syringe carrier and the plunger are rigidly connected for joint translation and rotation so that translation of the skin trigger sleeve into the depressed position results in translation of the plunger relative to the thrust tube resulting in rotation of the thrust tube about a small angle so that at least one bayonet pin is rotated out of a circumferential portion into a longitudinal portion of the at least one bayonet track.

4. The auto-injector according to claim 1, characterized in that a lock is arranged partially inside a distal end of a skin trigger sleeve around a piston rod of the plunger and axially coupled to the syringe carrier, wherein the piston rod is keyed into the lock for joint rotation, wherein the lock comprises at least one resilient arm engageable in a circumferential notch in the piston rod in a manner to couple the piston rod and the lock for joint translation, wherein the resilient arm is arranged to disengage from the circumferential notch due to ramped engagement under axial load, wherein the resilient arm is arranged to be outwardly supported by the skin trigger sleeve for preventing outward deflection thus coupling the plunger to the syringe carrier for needle insertion, wherein at least one aperture is arranged in the skin trigger sleeve for allowing outward deflection of the resilient arm upon the needle reaching an injection depth.

5. The auto-injector according to claim 4, characterized in that the resilient arm and the skin trigger sleeve are arranged to be splined to each other for joint rotation, wherein the spline engagement is interrupted by the aperture thus allowing rotation of the lock relative to the skin trigger sleeve upon the needle reaching the injection depth.

6. The auto-injector according to claim 5, characterized in that the aperture is arranged as an L-shaped aperture, wherein the spline engagement of the resilient arm and the skin trigger sleeve is interrupted by a second circumferential portion of the aperture, wherein a second longitudinal portion of the aperture is arranged to allow translation of the lock with the outwardly deflected and rotated resilient arm in distal direction relative to the skin trigger sleeve.

7. The auto-injector according to claim 6, characterized in that at least one lock boss is arranged on the lock for abutting against at least one stop on the skin trigger sleeve on rotation of the lock relative to the skin trigger sleeve thus preventing complete unscrewing of the plunger from the thrust tube.

8. The auto-injector according to claim 7, characterized in that the stop is arranged to be translated out of the way of the lock boss on removal of the auto-injector from the injection site and consequent translation of the skin trigger sleeve back into an advanced position so as to allow further rotation of the lock with the plunger for allowing complete unscrewing of the plunger and the thrust tube.

9. The auto-injector according to claim 4, characterized in that the retract collar is arranged to be coupled to the skin trigger sleeve for joint axial translation by a bayonet connection between an outward boss and an inward boss in the initial state, wherein upon release of the compression spring the retract collar is arranged to be rotated due to the corresponding fourth and fifth threads and the load of the compression spring transmitted via the plunger, the lock and the syringe carrier so as to disengage the bayonet connection and axially decouple the retract collar from the skin trigger sleeve.

10. The auto-injector according to claim 9, characterized in that a first detent for obstructing disengagement of the bayonet connection and a second detent for obstructing disengagement of a bayonet pin from a circumferential portion are arranged, wherein the first detent is configured to require more torque to be overcome than the second detent.

11. The auto-injector according to claim 4, characterized in that the aperture comprises a distal edge arranged to be engaged by the outwardly deflected resilient arm upon needle retraction so as to also retract the skin trigger sleeve into a depressed position.

* * * * *